(12) United States Patent
Mitelberg

(10) Patent No.: US 7,785,317 B2
(45) Date of Patent: Aug. 31, 2010

(54) JOINED METAL TUBING AND METHOD OF MANUFACTURE

(75) Inventor: Vladimir Mitelberg, Aventura, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 421 days.

(21) Appl. No.: 11/391,740

(22) Filed: Mar. 29, 2006

(65) Prior Publication Data

US 2007/0233039 A1  Oct. 4, 2007

(51) Int. Cl.
  *A61M 25/00* (2006.01)
(52) U.S. Cl. ................... 604/523; 604/95.01; 604/96.01
(58) Field of Classification Search ......... 604/523–532, 604/95.01–95.05, 96.01, 164.01
  See application file for complete search history.

(56) References Cited

U.S. PATENT DOCUMENTS

| | | | |
|---|---|---|---|
| 2,580,872 A | | 1/1952 | Wise |
| 3,128,536 A | * | 4/1964 | Eckhardt .................... 72/368 |
| 3,854,473 A | | 12/1974 | Matsuo |
| 4,215,703 A | | 8/1980 | Willson |
| 4,390,599 A | | 6/1983 | Broyles |
| 4,864,824 A | | 9/1989 | Gabriel et al. |
| 4,922,924 A | * | 5/1990 | Gambale et al. ............ 600/585 |
| 4,981,756 A | | 1/1991 | Rhandhawa |
| 4,994,032 A | | 2/1991 | Sugiyama et al. |
| 5,061,914 A | | 10/1991 | Busch et al. |
| 5,082,359 A | | 1/1992 | Kirkpatrick |
| 5,174,302 A | | 12/1992 | Palmer |
| 5,178,957 A | | 1/1993 | Kolpe et al. |
| 5,197,978 A | | 3/1993 | Hess |
| 5,288,230 A | | 2/1994 | Nikutowski et al. |
| 5,334,216 A | | 8/1994 | Vidal et al. |
| 5,360,397 A | | 11/1994 | Pinchuk |
| 5,403,700 A | | 4/1995 | Heller et al. |
| 5,437,288 A | | 8/1995 | Schwartz et al. |
| 5,543,019 A | | 8/1996 | Lee et al. |

(Continued)

FOREIGN PATENT DOCUMENTS

EP  0 641 224 B1  5/1993

(Continued)

OTHER PUBLICATIONS

U.S. Appl. No. 11/318,825, Wu.

(Continued)

*Primary Examiner*—Kevin C Sirmons
*Assistant Examiner*—Phillip Gray
(74) *Attorney, Agent, or Firm*—Cook Alex Ltd.

(57) ABSTRACT

A generally hollow article for use as or incorporation within a medical instrument navigable through body vessels of a human subject is provided. The article is defined by two metal pieces, such as nitinol and stainless steel, having different performance characteristics. At least a portion of the two pieces are arranged into an alternating pattern and joined together to define a joint or junction. The two pieces may each be provided as a tube having a spiral-cut section that is configured to be intermeshed with the spiral-cut section of the other metal. The article may also include a radiopaque material for improved placement within the body, which material may also be provided as a tube with a spiral-cut section to be intermeshed and joined with the first and second pieces.

4 Claims, 3 Drawing Sheets

U.S. PATENT DOCUMENTS

| | | | |
|---|---|---|---|
| 5,591,129 A | 1/1997 | Shoup et al. |
| 5,607,463 A | 3/1997 | Schwartz et al. |
| 5,629,077 A | 5/1997 | Turnlund et al. |
| 5,656,036 A | 8/1997 | Palmaz |
| 5,669,977 A | 9/1997 | Shufflebotham et al. |
| 5,681,575 A | 10/1997 | Burrell et al. |
| 5,685,961 A | 11/1997 | Pourrezaei et al. |
| 5,735,892 A | 4/1998 | Myers et al. |
| 5,744,958 A | 4/1998 | Werne |
| 5,753,251 A | 5/1998 | Burrell et al. |
| 5,762,615 A | 6/1998 | Weier |
| 5,766,710 A | 6/1998 | Turnlund et al. |
| 5,770,255 A | 6/1998 | Burrell et al. |
| 5,810,870 A | 9/1998 | Myers et al. |
| 5,843,289 A | 12/1998 | Lee et al. |
| 5,902,317 A | 5/1999 | Kleshinski et al. |
| 5,908,409 A | 6/1999 | Rinehart et al. |
| 5,925,038 A | 7/1999 | Panescu et al. |
| 5,925,075 A | 7/1999 | Myers et al. |
| 5,945,153 A | 8/1999 | Dearnaley |
| 5,947,940 A * | 9/1999 | Beisel ............... 604/526 |
| 5,951,586 A | 9/1999 | Berg et al. |
| 5,957,903 A | 9/1999 | Mitzaee et al. |
| 6,017,553 A | 1/2000 | Burrell et al. |
| 6,043,451 A | 3/2000 | Julien et al. |
| 6,096,175 A | 8/2000 | Roth |
| 6,113,557 A | 9/2000 | Fagan et al. |
| 6,174,329 B1 | 1/2001 | Callol et al. |
| 6,183,420 B1 | 2/2001 | Douk et al. |
| 6,203,732 B1 | 3/2001 | Clubb et al. |
| 6,238,686 B1 | 5/2001 | Burrell et al. |
| 6,319,277 B1 | 11/2001 | Rudnick et al. |
| 6,322,588 B1 | 11/2001 | Ogle et al. |
| 6,325,824 B2 | 12/2001 | Limon |
| 6,342,067 B1 | 1/2002 | Mathis et al. |
| 6,432,116 B1 | 8/2002 | Callister et al. |
| 6,436,132 B1 | 8/2002 | Patel et al. |
| 6,447,478 B1 | 9/2002 | Maynard |
| 6,471,721 B1 | 10/2002 | Dang |
| 6,527,919 B1 | 3/2003 | Roth |
| 6,533,905 B2 | 3/2003 | Johnson et al. |
| 6,537,310 B1 | 3/2003 | Palmaz et al. |
| 6,579,246 B2 | 6/2003 | Jacobsen et al. |
| 6,605,111 B2 | 8/2003 | Bose et al. |
| 6,620,172 B1 | 9/2003 | Dretler et al. |
| 6,627,246 B2 | 9/2003 | Mehta et al. |
| 6,645,243 B2 | 11/2003 | Vallana et al. |
| 6,652,508 B2 * | 11/2003 | Griffin et al. .............. 604/526 |
| 6,660,032 B2 | 12/2003 | Klumb et al. |
| 6,666,882 B1 | 12/2003 | Bose et al. |
| 6,726,993 B2 | 4/2004 | Teer et al. |
| 6,755,794 B2 | 6/2004 | Soukup |
| 6,786,920 B2 | 9/2004 | Shannon et al. |
| 6,805,898 B1 | 10/2004 | Wu et al. |
| 6,929,766 B2 | 8/2005 | Bartholomew |
| 2001/0020182 A1 | 9/2001 | Klumb et al. |
| 2001/0039449 A1 | 11/2001 | Johnson et al. |
| 2002/0032478 A1 | 3/2002 | Boekstegers et al. |
| 2002/0038143 A1 | 3/2002 | McCrea et al. |
| 2002/0072705 A1 | 6/2002 | Vrba et al. |
| 2002/0111667 A1 | 8/2002 | Girton et al. |
| 2002/0151958 A1 | 10/2002 | Chuter |
| 2003/0004567 A1 | 1/2003 | Boyle et al. |
| 2003/0065266 A1 | 4/2003 | Russell |
| 2003/0066533 A1 | 4/2003 | Loy |
| 2004/0098094 A1 | 5/2004 | Boyle et al. |
| 2004/0106913 A1 | 6/2004 | Eidenschink et al. |
| 2004/0143288 A1 | 7/2004 | Searle |
| 2004/0181174 A2 | 9/2004 | Davis et al. |
| 2005/0283134 A1 * | 12/2005 | Chan et al. .............. 604/523 |
| 2007/0149951 A1 * | 6/2007 | Wu et al. .............. 604/526 |

FOREIGN PATENT DOCUMENTS

| | | |
|---|---|---|
| EP | 0 824 900 B1 | 12/1996 |
| EP | 0 847 733 A1 | 12/1997 |
| EP | 1 099 004 A1 | 7/1999 |
| EP | 1 099 004 B1 | 7/1999 |
| EP | 1611914 A1 | 4/2006 |
| EP | 1709987 A | 11/2006 |
| GB | 2 331 998 A | 12/1998 |
| WO | WO 93/07924 | 4/1993 |
| WO | WO 93/23092 | 11/1993 |
| WO | WO 94/25637 | 11/1994 |
| WO | WO 95/13704 | 5/1995 |
| WO | WO 97/26026 | 7/1997 |
| WO | WO 99/66966 | 12/1999 |
| WO | WO 00/04204 | 1/2000 |

OTHER PUBLICATIONS

Pub Med Abstract from Spine, Jun. 1992; 17 (6 Suppl): S86-96 of Hellier, Hedman, Kostuik; Wear Studies for development of an intervertebral disc prosteses.

Pub Med Abstract from Biomaterials; Feb. 1993; 14(3):229-32 of LI; Behaviour of titanium and titania-based ceramics in vitro and in vivo.

Energy Database: ED1 Abstract from Banks et al.; Ion bombardment modification of surfaces in biomedical applications; Elsevier 399-434; 1984; Netherlands.

Engineering Index Database: EI1 Abstract from Advances in Bioengineering; Conference; Nov. 14, 1999; Nashville, TN, of USA; Chung, Chang, Han; Development of thin metal film deposition process for the intravascular catheter.

Engineering Index Database: EI1 Abstract of Journal of Materials Processing Technology; Kola, Daniels, Cameron, Hashmi; Magnetron sputtering of TiN protective coatings for medical applications; 422-430; Jan. 1996; Ireland.

Engineering Index Database: EI1 Abstract of Journal of Biomedical Materials Research; Yuhta et al.; Blood compatibility of sputter-deposited alumina films; 271-224; Feb. 1994.

Engineering Index Database: EI1 Abstract of Society for Biomaterials; Ong, Lucas, Lacefield, Rigney; Properties of calcium-phosphate coatings produced by ion-beam sputter deposition; Conference; May 1, 1991; US.

Medline Database (1993-1997): ME3 from Asaio J. Zabetakis, Cotell, Chrisey, Auyeung; Pulsed laser deposition of thin film hydroxyapatite. Applications for flexible catheters; 896-899; Jul. 1994; US.

European Patent Office, Communication, Extended European Search Report, Jun. 21, 2007.

* cited by examiner

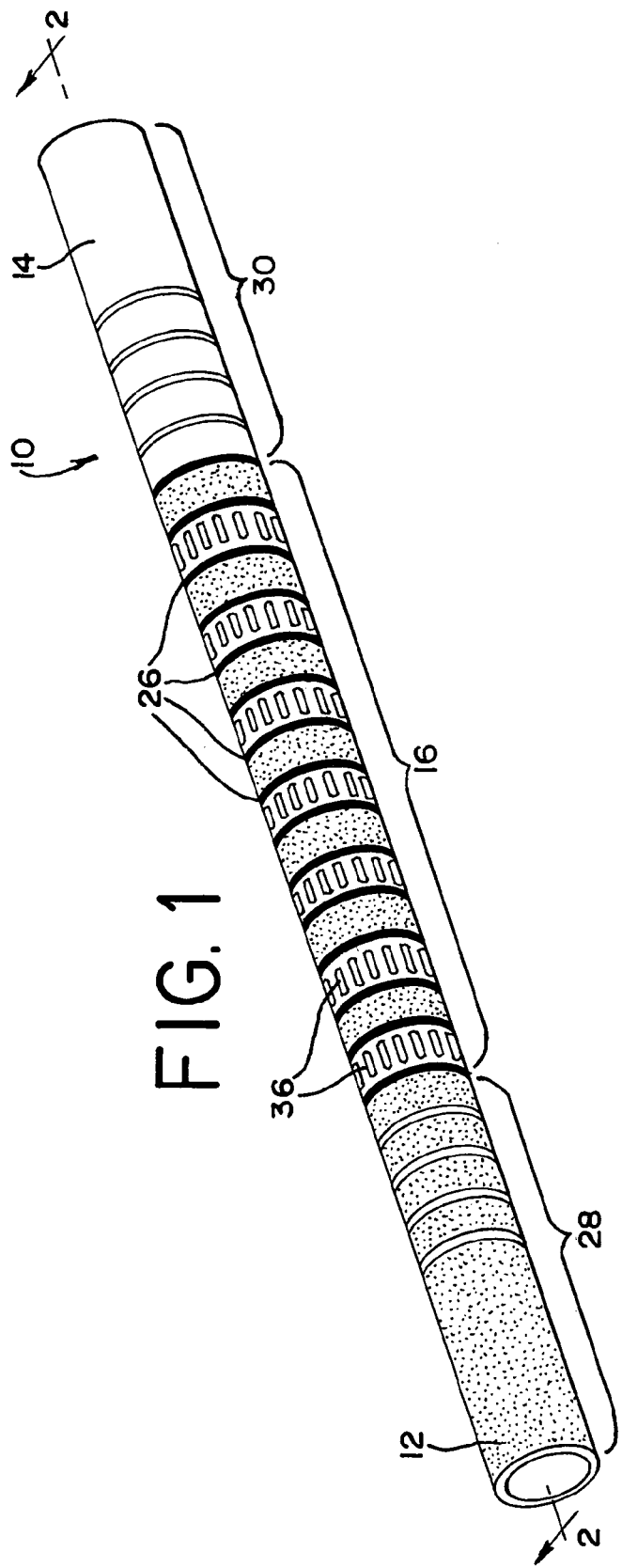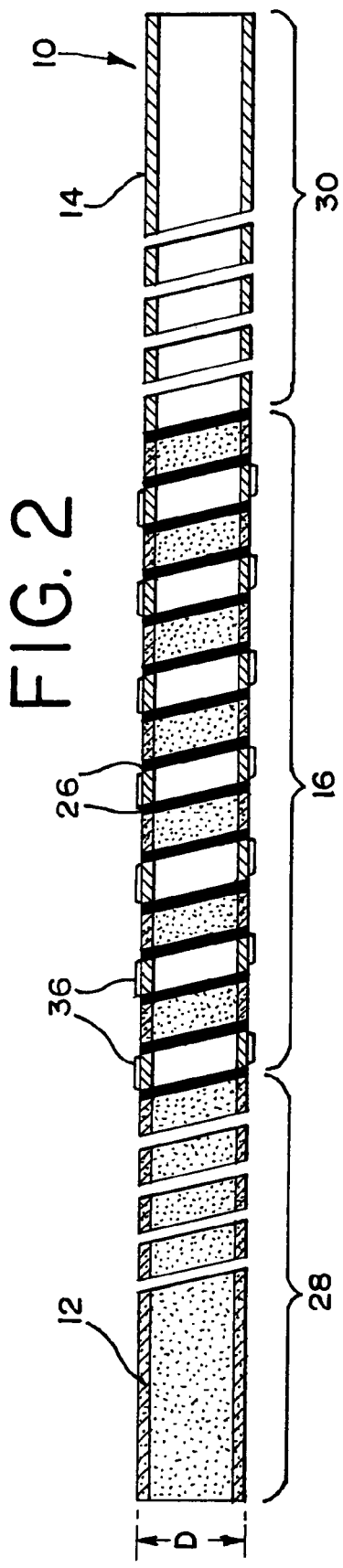

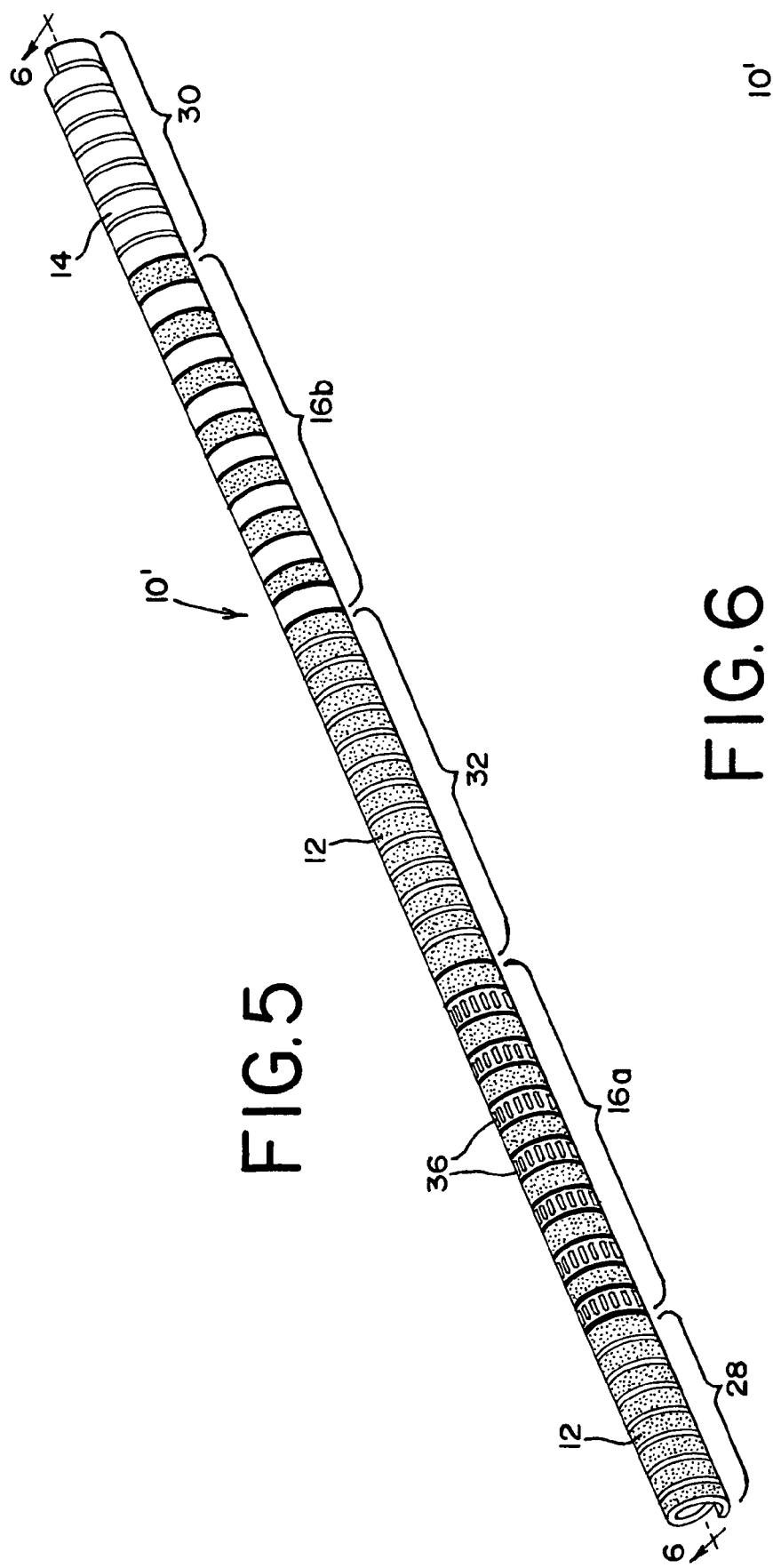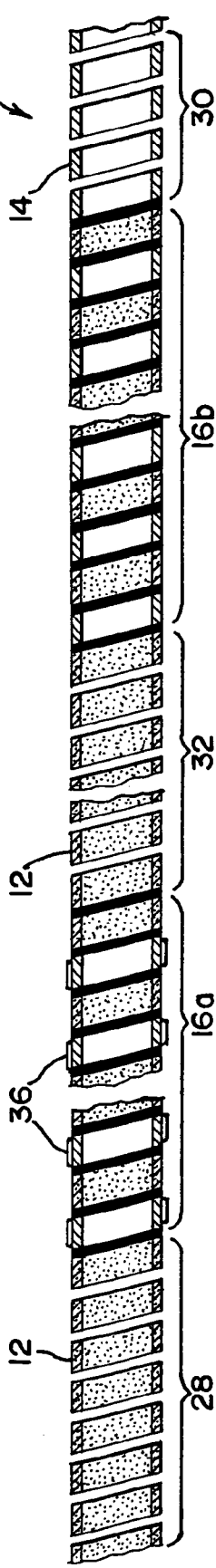

JOINED METAL TUBING AND METHOD OF MANUFACTURE

FIELD OF THE INVENTION

This invention generally relates to medical devices that are navigable through body vessels of a human subject. More particularly, this invention relates to tubular devices formed from at least two separate metal pieces.

DESCRIPTION OF RELATED ART

A number of medical procedures require the introduction of tubing to a body vessel. For example, vessel defects, such as blockages and stenoses, within the human vasculature system are often treated by the intraluminal delivery of treatment fluids or expansion devices and stents. Expansion devices can take any of a number of forms, but are all generally delivered by a flexible catheter that, once properly positioned, deploys the expansion device. The path to the diseased site is typically tortuous and may additionally pass through other constricted lumens, so catheters generally cannot be used to define their own path through the vasculature. As such, a more rigid guidewire is first passed through the vasculature to the desired site, then the catheter is passed over the guidewire.

The different body environments in which guidewires must operate create several design complications. For example, it is desirable for the guidewire to be somewhat flexible so that it can pass through tortuous portions of the vasculature. On the other hand, it is also desirable for the guidewire to be somewhat rigid so that it may be forced through constricted body vessels and lesions or used to perforate the fibrocalcific cap of chronic total coronary artery occlusions. More rigid guidewires also provide tactile feedback to the operator. Most guidewires have a fixed stiffness, so the surgeon must select a guidewire based on the predicted body environment. Of course, if the guidewire is not properly selected, then multiple guidewires with different stiffnesses must be used. Even proper guidewire selection cannot obviate the need for multiple guidewire usage for some body environments.

In recognition of this problem, a number of variable stiffness guidewires and stylets have been suggested. Examples can be seen in U.S. Pat. No. 3,854,473 to Matsuo; U.S. Pat. No. 4,215,703 to Willson; U.S. Pat. No. 5,762,615 to Weier; U.S. Pat. No. 5,957,903 to Mirzaee et al.; U.S. Pat. No. 6,113,557 to Fagan et al; U.S. Pat. No. 6,183,420 to Douk et al.; and U.S. Pat. No. 6,755,794 to Soukup, all of which are hereby incorporated herein by reference.

Generally speaking, these variable stiffness devices include a tube which receives a corewire that protrudes distally beyond the tube. A coiled spring surrounds the protruding portion and is connected at opposite ends to the corewire and the tube, such that axial movement of the corewire with respect to the tube will compress or stretch the spring. When the tip of the corewire is moved away from the tube using a handle outside of the body, the separation gaps between the coils of the spring enlarge and the tip become more flexible and better suited for being fed through tortuous body vessels. In the event that the guidewire encounters a constricted body vessel through which it must pass, the corewire is moved toward the tube, which compresses the spring and causes the separation gaps to diminish and the tip to become more rigid.

While these known variable stiffness guidewires are an improvement over previous fixed stiffness guidewires, there are still several possible areas of improvement. For example, the described tubes are comprised of a relatively rigid material, typically stainless steel. Stainless steel is well-suited for procedures requiring the guidewire to be forced through a constricted vessel, but it is not sufficiently flexible for procedures requiring the guidewire to define a tortuous path.

One approach to this problem can be found in U.S. patent application Ser. No. 11/318,825 to Wu, which is hereby incorporated herein by reference. Wu describes the use of a tube comprising a stainless steel proximal portion and a nitinol distal portion that are connected at a joint. Numerous joinder methods are described, including crimping, swaging, welding, brazing, and soldering. While these methods are adequate for joining different tube materials, they generally involve a relatively small joinder region. In keeping with the invention, it has been developed that an improved joint can be achieved by providing a method resulting in a larger joinder region.

Metallic tubing is used in numerous other intraluminal devices, such as components in catheters for balloon angioplasty or in fluid infusion catheters or in embolic coil/implant detachment systems. Those of ordinary skill in the art will appreciate that the above-described problems are present in many applications involving these types of devices, and wherein it would be desirable to provide tubing with sections having different performance characteristics along its length.

SUMMARY OF THE INVENTION

In accordance with one aspect of the present invention, a generally hollow device is provided with a first piece and a second piece. The first piece is substantially comprised of a first metal and the second piece is substantially comprised of a different second metal. The first metal can be more flexible at body temperature than the second metal. The two pieces are joined in a generally alternating pattern in order to define a tubular portion of the device.

According to another aspect of the present invention, a method of creating a generally hollow device includes providing first and second tubes substantially comprised of different metals. The first metal can be more flexible at body temperature than the second metal. Each tube includes a spiral cut section, which sections are arranged into a generally alternating pattern. At least a portion of each of the alternating spiral-cut sections is joined to define a tubular portion of the device.

Special application for the present invention has been found for tubular portions of guidewires, catheters, and embolic coil/implant detachment systems. The invention may be used, for example, in numerous intraluminal devices, such as components in catheters for balloon angioplasty, in guiding catheters or in fluid infusion catheters or in embolic coil and/or implant delivery and/or detachment systems. However, the present invention is also applicable to tubular components of other devices adapted for movement through body lumens, so it will be understood that the products and methods described herein are not limited to particular medical devices or particular surgical applications.

Accordingly, a general aspect or object of the present invention is to provide a tubular medical device that incorporates a plurality of separate metals having different performance characteristics.

Another aspect or object of this invention is to provide a tubular medical device with an improved joint for joining a plurality of separate metals.

Another aspect or object of this invention is to provide a method of manufacturing a tubular medical device with an improved joint for joining a plurality of separate metals.

Another aspect or object of this invention is to provide a method and improved joint for tubular medical devices without increasing the diameter of the tubing thus joined together.

Other aspects, objects and advantages of the present invention, including the various features used in various combinations, will be understood from the following description according to preferred embodiments of the present invention, taken in conjunction with the drawings in which certain specific features are shown.

BRIEF DESCRIPTION OF THE DRAWINGS

FIG. 1 is a front elevational view of a medical device portion according to an aspect of the present invention;

FIG. 2 is a cross-sectional view of the medical device portion of FIG. 1, taken through the line 2-2 of FIG. 1;

FIG. 5 is a front elevational view of a medical device portion according to a further embodiment of the present invention; and FIG. 6 is a cross-sectional view of the medical device portion of FIG. 5, taken through the line 6-6 of FIG. 5.

DESCRIPTION OF THE PREFERRED EMBODIMENTS

Figure 3:
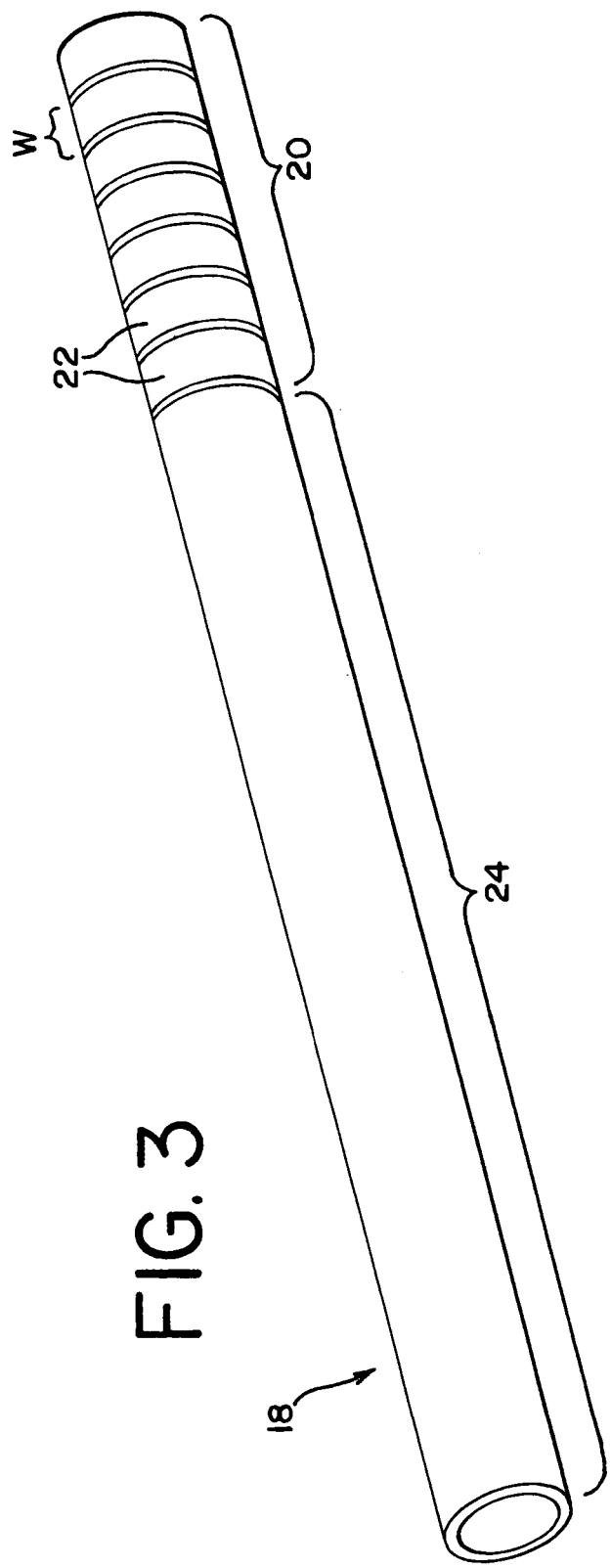
FIG. 3 is a front elevational view of a metal tube suitable for use in manufacturing a medical device according to the present invention.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1 and 2 illustrate a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular article, member or device is generally designated at 10 and shown as a substantially right cylindrical structure. However, the tubular device 10 may have a tapered or curved outer surface without departing from the scope of the present invention. The tubular device 10 is adapted to be received by a body vessel as a component or part of a medical device guidewire, detachment system, deployment system or catheter or other medical instrument or device as generally discussed herein.

The illustrated tubular device 10 is comprised of two separate metal pieces 12 and 14, substantially comprised of different metals having different performance characteristics, that are joined at an elongated joint or junction 16. When used herein, the term "join" and its derivatives refer to affixation of at least a portion of the first piece 12 to the second piece 14 at the joint 16. Providing the two pieces 12 and 14 in an alternating pattern without affixing them to each other is insufficient, because the pieces 12 and 14 can separate from each other, thereby dissolving the joint 16. Furthermore, if the pieces 12 and 14 are not sealed together at the joint 16, then the open seams therebetween will prevent the tubular device 10 from performing a number of common applications, such as fluid transfer, guidance, and containment. In addition, merely wrapping one piece around the other at the joint is insufficient and has the negative effect of increasing the outer diameter D of the tubular device 10, which increased size makes it more difficult to maneuver the device 10 through a body vessel.

The first and second pieces 12 and 14 each typically has a construction along the lines of a tube 18, illustrated in FIG. 3, having a spiral-cut section 20 that defines a plurality of coils 22. While a substantially helical incision is preferred, it will be understood by those of ordinary skill in the art that the spiral-cut section 20 need not be defined by a strictly helical incision, but other shapes may be practiced without departing from the scope of the present invention. Hence, when used herein, the term "spiral-cut section" does not limit the tube 18 to a particular geometry.

Any of a number of cutting methods may be employed to create the spiral-cut section 20, depending on the metal itself, the metal to which it will be joined, the joinder means to be employed, the thickness of the tube 18, the intended use of the device 10 ultimately produced, the machinery available, cost and time constraints, and other factors. Selection of a suitable cutting method based on these factors is within the capabilities of one of ordinary skill in the art.

The spiral-cut section 20 may be a discrete region of the tube 18, at an end or somewhere between the ends, but it may also extend along the length of the tube 18, such that the tube resembles a helical coil. However, the pieces 12 and 14 typically are not provided as a typical manufactured helical coil, i.e., drawn or cold-worked or wound, for a number of reasons. These are exemplified by the following. First, it is more difficult to manufacture a satisfactory coil of the appropriate size than a tube of the same size. Second, it is much easier to create coils having a varying width W or an irregular shape by the present invention than by typical coil-forming methods. Third, an improved mating relationship between the first and second pieces 12 and 14 is possible by custom cutting spiral-cut sections 20 that are specially suited for joinder with each other. Fourth, it is easier to create a tube 18 with cut sections 20 and uncut sections 24 by the present invention than by combining a coil with a typical tube. However, although it is not preferred to use a commercially available helical coil, it is within the scope of the present invention to use such a coil in combination with a tube 18 according to the preceding description.

Referring back to FIGS. 1 and 2, the joint 16 is a tubular portion that is characterized by the two pieces 12 and 14 being arranged in a generally alternating pattern. As with the spiral-cut sections 20, the joint 16 may have a tapered or curved profile without departing from the scope of the present invention. Preferably, the respective spiral-cut sections 20 of the first and second metal tubes are configured such that they can be combined into the pattern of FIGS. 1 and 2. The intermeshed portions of the two pieces 12 and 14 define a single layer, best illustrated in FIG. 2, and are joined together at the joint 16 by a suitable means, such as solder or adhesive, which is designated at 26. Preferably, the respective outer and inner diameters of the two pieces 12 and 14 are substantially identical due to performance and manufacturing concerns, which are described in greater detail herein. It will be appreciated by those of ordinary skill in the art that the alternating pattern results in a larger joinder region than would typically be achieved by joining two separate pieces using known means, such as a butt weld. Thus, a device according to the present invention is able to achieve a more durable joint without disadvantageously increasing the outer diameter.

Figure 4:
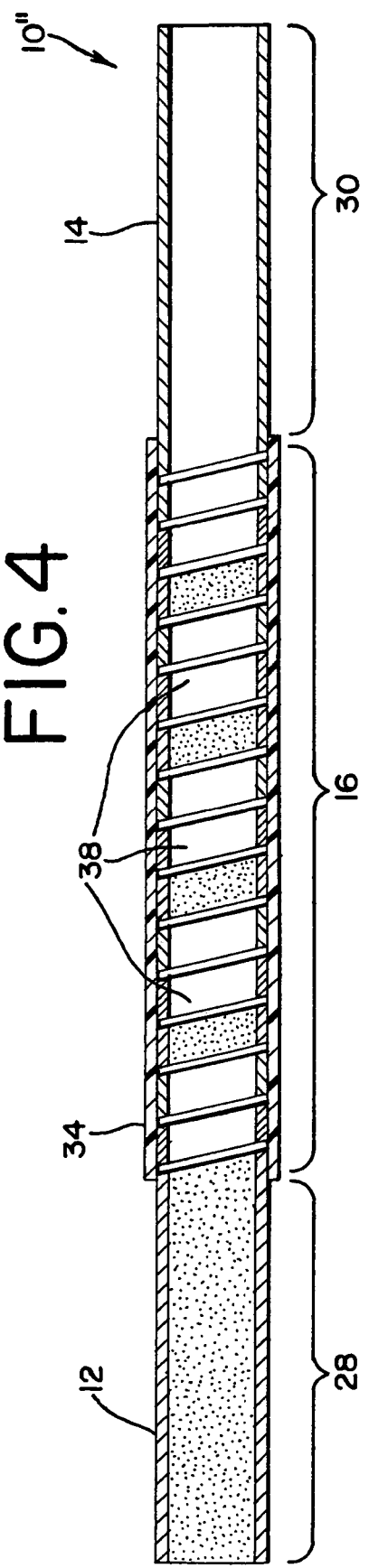
FIG. 4 is a cross-sectional view of a medical device portion according to another embodiment of the present invention.

As illustrated in FIGS. 1 and 2, the joint 16 is typically located at a discrete region between the ends of the device 10, which region separates a first section 28, substantially defined by a portion of the first piece 12, and a second section 30, substantially defined by a portion of the second piece 14. The first and second sections 28 and 30 typically correspond to the uncut section 24 of the tube 18 of FIG. 3, as shown in FIG. 4 but, as shown in FIGS. 1 and 2, they may be at least partially spiral-cut. Of course, the specific geometry and composition of the first and second sections 28 and 30 will depend on the nature of the medical instrument in which the tubular device 10 will eventually be incorporated.

The first section 28 will exhibit performance characteristics of the first metal, the second section 30 will exhibit performance characteristics of the second metal, and the joint 16 will exhibit a variation of the performance characteristics of the first and second metals. Some or all of the turns of one metal may be wider than the turns of the other metal, such that the joint 16 will exhibit performance characteristics more similar to one metal (typically the metal tube having the wider turns) than the other.

In a preferred embodiment the first metal has superelastic properties. When used herein, the term "superelastic" is intended to refer to materials that typically exhibit both martensitic and austenitic properties and that have austenitic properties in use. More preferably, the first metal is a nitinol material having superelastic properties. Most preferably, the nitinol composition has a transformation temperature lower than body temperature, such that the nitinol material is in a austentic state when in use in vivo. Preferably, the second metal is stainless steel, in which case the first metal is more flexible than the second metal at human body temperature.

The device may be provided in a number of variations, such as by providing a plurality of discrete joints 16 spaced along its length. For example, FIGS. 5 and 6 illustrate a tubular device 10' having a first joint 16a and a second joint 16b that are separated by an intermediate section 32. The intermediate section 32 may be cut, as illustrated in FIGS. 5 and 6, or uncut and be a part of either the first piece 12, as illustrated in FIGS. 5 and 6, or the second piece 14. In another embodiment, the joint 16 may define the entire length of the tubular device, in which case the entire device will exhibit a combination of the performance characteristics of the first and second metals. In yet another embodiment, the joint 16 and/or other portions of the tubular device may be tapered or curved, rather than having the generally uniform, right cylindrical outer diameter of FIGS. 1 and 2. In still another embodiment, illustrated in FIG. 4, a tubular device 10'' may be provided with a length of shrink tubing 34 instead of the joinder means 26 of FIGS. 1 and 2 to join the first and second pieces 12 and 14. If shrink tubing 34 is used, then it is preferably selected to provide a fluid seal to allow the joint 16 to perform a wider variety of functions, such as fluid injection and containment.

Preferably, the device is provided with a radiopaque material to allow for improved positioning of a device within the body. There are several ways to provide the radiopaque material. For example, as illustrated in FIGS. 1 and 2, radiopaque bars or rivets 36 may be placed into or onto one or both of the pieces 12 and 14 before or after they are joined. FIG. 4 shows a preferred embodiment in which a third piece 38 is provided that is substantially comprised of a radiopaque material. In the illustrated embodiment, the third piece 38 is joined to the first and second pieces 12 and 14 at the joint 16 in an alternating pattern. It will be appreciated that this is similar to the alternating pattern of FIGS. 1 and 2, except that three pieces are intermeshed instead of just two. The use of a third piece 38 rather than bars or rivets 36 may be preferred, because it may be incorporated without increasing the outer diameter D of the device. The third piece 38, whether provided as a tube 18 according to FIG. 3 or as a filament or coil or the like, may be less elongated than the first and second pieces 12 and 14, such that the radiopaque material resides wholly or primarily within the joint 16. Preferably, the radiopaque material is a metal, such as platinum.

In order to assemble the device, at least a portion of the first piece 12 and the second piece 14 and, if provided, the third piece 38 are intermeshed. This is typically accomplished by stretching the spiral-cut sections 20, thereby increasing their pitch and allowing them to be fit together in a single-layer, alternating pattern that defines the joint 16. Then, the portions of the spiral-cut sections 20 within the joint 16 are joined by suitable means.

Preferably, this process is performed with the aid of a mandrel, not illustrated, that is received by the device 10. The mandrel may be placed within the lumen of the device 10 before or after the spiral-cut sections 20 are intermeshed, but it should be in place before they are joined. The mandrel ensures that the lumen remains open during and after joinder. The mandrel typically is circular in cross-section, but may be tapered, curved, or irregularly shaped in order to conform to the final shape or cross-section needed for the tubular device 10. Those of ordinary skill in the art will appreciate that formation of the joint 16 on the mandrel can be simplified by providing pieces 12 and 14 with substantially identical outer and inner diameters, because the pieces 12 and 14 will lay smoothly and evenly over the mandrel.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A hollow tubular article for a medical device adapted to be received by a body vessel, comprising:
   a first hollow tube piece substantially comprised of a first metal, said first hollow tube piece is a first tube of said first metal, the first tube having a solid tube section and a first spiral cut-out section;
   a second hollow tube piece substantially comprised of a second metal, said second hollow tube piece is a second tube of said second metal, the second tube having a solid tube section and a second spiral cut-out section, wherein the first spiral cut-out section and the second spiral cut-out section define a spiral space therebetween;
   said first metal is different from and more flexible at human body temperature than said second metal;
   a third hollow piece substantially comprised of a radiopaque material, said third hollow piece being within said spiral space such that the first spiral cut-out section, the second spiral cut-out section and the third hollow piece within the spiral space form a joint longitudinally between the first hollow tube piece and the second hollow tube piece;
   said first and second spiral cut-out sections have substantially identical outer diameters and substantially identical inner diameters, said third hollow piece has an outer diameter no greater than said outer diameter of the cut-out sections, and said third hollow piece has an inner diameter no smaller than said inner diameter of the cut-out sections;
   the joint further includes a shrink tubing along said spiral cut-out sections and said third hollow piece, and the shrink tubing adheres together the first and second hollow tube pieces so as to seal together the first and second cut-out sections along with said third hollow piece.

2. The article of claim 1, wherein said first metal has superelastic properties.

3. The article of claim 1, wherein said first metal is a nitinol material.

4. The article of claim 1, wherein said first metal is a nitiriol material and said second metal is stainless steel.

* * * * *